(12) United States Patent
Fixman et al.

(10) Patent No.: US 7,829,528 B2
(45) Date of Patent: Nov. 9, 2010

(54) COMPOSITIONS AND METHODS FOR TREATING STAT-6 ASSOCIATED DISEASES OR CONDITIONS

(75) Inventors: Elizabeth D. Fixman, Montreal (CA); Christine T. McCusker, Montreal (CA)

(73) Assignee: The Rockefeller University, New York, NY (US)

( * ) Notice: Subject to any disclaimer, the term of this patent is extended or adjusted under 35 U.S.C. 154(b) by 355 days.

(21) Appl. No.: 11/575,164

(22) PCT Filed: Sep. 12, 2005

(86) PCT No.: PCT/US2005/032948

§ 371 (c)(1),
(2), (4) Date: Mar. 31, 2007

(87) PCT Pub. No.: WO2006/031976

PCT Pub. Date: Mar. 23, 2006

(65) Prior Publication Data

US 2008/0113909 A1 May 15, 2008

Related U.S. Application Data

(60) Provisional application No. 60/609,884, filed on Sep. 14, 2004.

(51) Int. Cl.
*C07K 14/00* (2006.01)
(52) U.S. Cl. .......................................... 514/2; 530/350
(58) Field of Classification Search ................ 514/2; 530/350
See application file for complete search history.

(56) References Cited

U.S. PATENT DOCUMENTS

| 6,207,391 B1 | 3/2001 | Wu et al. |
| 6,368,828 B1 | 4/2002 | LaRochelle et al. |
| 6,426,331 B1 | 7/2002 | McKinney et al. |

2003/0186841 A1   10/2003   Barhas, III et al.

FOREIGN PATENT DOCUMENTS

| WO | WO0183517 | 11/2001 |
| WO | WO0238107 | 5/2002 |

OTHER PUBLICATIONS

Lu et al. 1997; Identification of STAT6 domain required for IL-4 activation of transcription. Journal of Immunology. 159: 1255-1264.*
Calo et al., "STAT Proteins:From Normal Control of Cellular Events to Tumorigenesis", Journal of Cellular Physiology 2003 197:157-168.
Heim et al., "Contribution of STAT SH2 Groups to Specific Interferon Signaling by the Jak-STAT Pathway", Science 1995 267:1347-1349.
Khurana et al., "IL-13 receptors and signaling pathways: An evolving web", J. Allergy Clin Immunol 2003 111:677-690.
Hirayama et al., "Inhibition of Inflammatory Bone Erosion by Constitutively Active STAT-6 Through Blockade of JNK and NF-kB Activation", Arthritis & Rheumatism 2005 52(9):2719-2729.
Ho et al., "Synthetic Protein transduction Domains:Enhanced Transduction Potential in Vitro and in Vivo", Cancer Research 2001 61:474-477.
Songyang at al., SH2 Domains Recognize Specific Phosphopeptide Sequences, Cell 1993 72:767-778.
Stolzenberger et al., "Specific inhibition of interleukin-4-dependent Stat6 activation by an intracellularly delivered peptide", Eur. J. Biochem. 2001 268:4809-4814.

* cited by examiner

*Primary Examiner*—Karen Cochrane Carlson
(74) *Attorney, Agent, or Firm*—Licata & Tyrrell P.C.

(57) ABSTRACT

The present invention relates to a cell permeable peptide to specifically inhibit tyrosine phosphorylation and/or subsequent activation of STAT-6. This peptide is composed of a protein transduction moiety operably linked to a portion of STAT-6 which contains tyrosine residue 641 (Tyr-641) of STAT-6, wherein Tyr-641 is phosphorylated. The chimeric STAT-6 peptide enters cells and binds to the SH2 domain of wild-type STAT-6, and subsequently inhibits dimerization and nuclear translocation of the wild-type STAT-6 protein. Administration of this chimeric peptide inhibits allergen-induced airway inflammation, cytokine production and airway hyperresponsiveness and is useful in methods for preventing or treating diseases or conditions associated with STAT-6 activation.

3 Claims, No Drawings

```
                           SEQUENCE LISTING

<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: "Xaa" represents amino acid residues Lys, Val,
      Arg, Ile, or Met.
<220> FEATURE:
<221> NAME/KEY: MISC_FEATURE
<222> LOCATION: (3)..(3)
<223> OTHER INFORMATION: "Xaa" represents amino acid residues Pro, Ala,
      or Ser.
<220> FEATURE:
<221> NAME/KEY: MISC_FEATURE
<222> LOCATION: (4)..(4)
<223> OTHER INFORMATION: "Xaa" represents amino acid residues Trp, Tyr,
      Phe, His, or Leu.

<400> SEQUENCE: 1

Tyr Xaa Xaa Xaa
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Tyr Val Ser Thr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Tyr Val Pro Ala
1

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Gly Arg Gly Tyr Val Ser Thr Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 5

Gly Arg Gly Tyr Val Pro Ala Thr
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Tyr Ala Arg Ala Ala Ala Arg Gln Ala Arg Ala
1               5                   10

<210> SEQ ID NO 7
<211> LENGTH: 19
<212> TYPE: PRT
<213> ORGANISM: Artificial Sequence
<220> FEATURE:
<223> OTHER INFORMATION: Synthetic peptide

<400> SEQUENCE: 7

Tyr Ala Arg Ala Ala Ala Arg Gln Ala Arg Ala Gly Arg Gly Tyr Val
1               5                   10                  15

Ser Thr Thr

<210> SEQ ID NO 8
<211> LENGTH: 19
<212> TYPE: PRT
<213> ORGANISM: Artificial Sequence
<220> FEATURE:
<223> OTHER INFORMATION: Synthetic peptide

<400> SEQUENCE: 8

Tyr Ala Arg Ala Ala Ala Arg Gln Ala Arg Ala Gly Arg Gly Phe Val
1               5                   10                  15

Ser Thr Thr

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Tyr Gly Arg Lys Lys Arg Arg Gln Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Tyr Ala Arg Lys Ala Arg Arg Gln Ala Arg Arg
1               5                   10

<210> SEQ ID NO 11
<211> LENGTH: 11
<212> TYPE: PRT
<213> ORGANISM: Artificial Sequence
```

```
<220> FEATURE:
<223> OTHER INFORMATION: Synthetic peptide

<400> SEQUENCE: 11

Tyr Ala Arg Ala Ala Arg Arg Ala Ala Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Tyr Ala Arg Ala Ala Arg Arg Ala Ala Arg Ala
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Tyr Ala Arg Arg Arg Arg Arg Arg Arg Arg
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
gctagttgtc atcctgctc                                              19

<210> SEQ ID NO 17
<211> LENGTH: 19
<212> TYPE: DNA
```

```
<213> ORGANISM: Artificial Sequence
<220> FEATURE:
<223> OTHER INFORMATION: Synthetic oligonucleotide

<400> SEQUENCE: 17
gtgatgtgga cttggactc                                                    19

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
gccagcccac agttctacag c                                                 21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
gtgatgttgc tcagctcctc a                                                 21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
tggctctgca ggattttcat g                                                 21

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
tcaagtggca tagatgtgga agaa                                              24

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gccatggact gtggtcatga                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ttcaccacca tggagaaggc                                                   20
```

```
<210> SEQ ID NO 24
<211> LENGTH: 837
<212> TYPE: PRT
<213> ORGANISM: Mus musculus

<400> SEQUENCE: 24

Met Ser Leu Trp Gly Leu Ile Ser Lys Met Ser Pro Glu Lys Leu Gln
1               5                   10                  15

Arg Leu Tyr Val Asp Phe Pro Gln Arg Leu Arg His Leu Leu Ala Asp
            20                  25                  30

Trp Leu Glu Ser Gln Pro Trp Glu Phe Leu Val Gly Ser Asp Ala Phe
        35                  40                  45

Cys Tyr Asn Met Ala Ser Ala Leu Leu Ser Ala Thr Val Gln Arg Leu
    50                  55                  60

Gln Ala Thr Ala Gly Glu Gln Gly Lys Gly Asn Ser Ile Leu Pro His
65                  70                  75                  80

Ile Ser Thr Leu Glu Ser Ile Tyr Gln Arg Asp Pro Leu Lys Leu Val
                85                  90                  95

Ala Thr Ile Arg Gln Ile Leu Gln Gly Glu Lys Lys Ala Val Ile Glu
            100                 105                 110

Glu Phe Arg His Leu Pro Gly Pro Phe His Arg Lys Gln Glu Glu Leu
        115                 120                 125

Lys Phe Thr Thr Pro Leu Gly Arg Leu His His Arg Val Arg Glu Thr
    130                 135                 140

Arg Leu Leu Arg Glu Ser Leu His Leu Gly Pro Lys Thr Gly Gln Val
145                 150                 155                 160

Ser Leu Gln Asn Leu Ile Asp Pro Pro Leu Asn Gly Pro Gly Pro Ser
                165                 170                 175

Glu Asp Leu Pro Thr Ile Leu Gln Gly Thr Val Gly Asp Leu Glu Thr
            180                 185                 190

Thr Gln Pro Leu Val Leu Leu Arg Ile Gln Ile Trp Lys Arg Gln Gln
        195                 200                 205

Gln Leu Ala Gly Asn Gly Thr Pro Phe Glu Glu Ser Leu Ala Gly Leu
    210                 215                 220

Gln Glu Arg Cys Glu Ser Leu Val Glu Ile Tyr Ser Gln Leu His Gln
225                 230                 235                 240

Glu Ile Gly Ala Ala Ser Gly Glu Leu Glu Pro Lys Thr Arg Ala Ser
                245                 250                 255

Leu Ile Ser Arg Leu Asp Glu Val Leu Arg Thr Leu Val Thr Ser Ser
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Gln Phe Leu Gly Thr
    290                 295                 300

Ser Thr Lys Pro Pro Met Val Arg Ala Asp Met Val Thr Glu Lys Gln
305                 310                 315                 320

Ala Arg Glu Leu Ser Leu Ser Gln Gly Pro Gly Thr Gly Val Glu Ser
                325                 330                 335

Thr Gly Glu Ile Met Asn Asn Thr Val Pro Leu Glu Asn Ser Ile Pro
            340                 345                 350

Ser Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
```

-continued

```
            370                 375                 380
Ala Val Leu Phe Ser Thr Ser Phe Thr Leu Gly Pro Asn Lys Leu Leu
385                 390                 395                 400

Ile Gln Leu Gln Ala Leu Ser Leu Ser Leu Val Val Ile Val His Gly
                    405                 410                 415

Asn Gln Asp Asn Asn Ala Lys Ala Thr Ile Leu Trp Asp Asn Ala Phe
                    420                 425                 430

Ser Glu Met Asp Arg Val Pro Phe Val Val Gly Glu Arg Val Pro Trp
            435                 440                 445

Glu Lys Met Cys Glu Thr Leu Asn Leu Lys Phe Met Val Glu Val Gly
450                 455                 460

Thr Ser Arg Gly Leu Leu Pro Glu His Phe Leu Phe Leu Ala Gln Lys
465                 470                 475                 480

Ile Phe Asn Asp Asn Ser Leu Ser Val Glu Ala Phe Gln His Arg Cys
                    485                 490                 495

Val Ser Trp Ser Gln Phe Asn Lys Glu Ile Leu Leu Gly Arg Gly Phe
                    500                 505                 510

Thr Phe Trp Gln Trp Phe Asp Gly Val Leu Asp Leu Thr Lys Arg Cys
            515                 520                 525

Leu Arg Ser Tyr Trp Ser Asp Arg Leu Ile Ile Gly Phe Ile Ser Lys
530                 535                 540

Gln Tyr Val Thr Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
                    565                 570                 575

Ile Arg Gly Gln Asp Gly Ser Ser Gln Ile Glu Asn Ile Gln Pro Phe
                    580                 585                 590

Ser Ala Lys Asp Leu Ser Ile Arg Ser Leu Gly Asp Arg Ile Arg Asp
            595                 600                 605

Leu Ala Gln Leu Lys Asn Leu Tyr Pro Lys Lys Pro Lys Asp Glu Ala
610                 615                 620

Phe Arg Ser His Tyr Lys Pro Glu Gln Met Gly Lys Asp Gly Arg Gly
625                 630                 635                 640

Tyr Val Ser Thr Thr Ile Lys Met Thr Val Glu Arg Asp Gln Pro Leu
                    645                 650                 655

Pro Thr Pro Glu Pro Gln Met Pro Ala Met Val Pro Pro Tyr Asp Leu
                    660                 665                 670

Gly Met Ala Pro Asp Ala Ser Met Gln Leu Ser Ser Asp Met Gly Tyr
            675                 680                 685

Pro Pro Gln Ser Ile His Ser Phe Gln Ser Leu Glu Glu Ser Met Ser
690                 695                 700

Val Leu Pro Ser Phe Gln Glu Pro His Leu Gln Met Pro Pro Asn Met
705                 710                 715                 720

Ser Gln Ile Thr Met Pro Phe Asp Gln Pro His Pro Gln Gly Leu Leu
                    725                 730                 735

Gln Cys Gln Ser Gln Glu His Ala Val Ser Ser Pro Glu Pro Met Leu
                    740                 745                 750

Trp Ser Asp Val Thr Met Val Glu Asp Ser Cys Leu Thr Gln Pro Val
            755                 760                 765

Gly Gly Phe Pro Gln Gly Thr Trp Val Ser Glu Asp Met Tyr Pro Pro
770                 775                 780

Leu Leu Pro Pro Thr Glu Gln Asp Leu Thr Lys Leu Leu Leu Glu Asn
785                 790                 795                 800
```

```
Gln Gly Glu Gly Gly Ser Leu Gly Ser Gln Pro Leu Leu Lys Pro
                805                 810                 815

Ser Pro Tyr Gly Gln Ser Gly Ile Ser Leu Ser His Leu Asp Leu Arg
            820                 825                 830

Thr Asn Pro Ser Trp
        835

<210> SEQ ID NO 25
<211> LENGTH: 847
<212> TYPE: PRT
<213> ORGANISM: Homo sapiens

<400> SEQUENCE: 25

Met Ser Leu Trp Gly Leu Val Ser Lys Met Pro Glu Lys Val Gln
  1               5                  10                  15

Arg Leu Tyr Val Asp Phe Pro Gln His Leu Arg His Leu Leu Gly Asp
                 20                  25                  30

Trp Leu Glu Ser Gln Pro Trp Glu Phe Leu Val Gly Ser Asp Ala Phe
             35                  40                  45

Cys Cys Asn Leu Ala Ser Ala Leu Leu Ser Asp Thr Val Gln His Leu
 50                  55                  60

Gln Ala Ser Val Gly Glu Gln Gly Glu Gly Ser Thr Ile Leu Gln His
 65                  70                  75                  80

Ile Ser Thr Leu Glu Ser Ile Tyr Gln Arg Asp Pro Leu Lys Leu Val
                 85                  90                  95

Ala Thr Phe Arg Gln Ile Leu Gln Gly Glu Lys Lys Ala Val Met Glu
                100                 105                 110

Gln Phe Arg His Leu Pro Met Pro Phe His Trp Lys Gln Glu Glu Leu
            115                 120                 125

Lys Phe Lys Thr Gly Leu Arg Arg Leu Gln His Arg Val Gly Glu Ile
130                 135                 140

His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
            245                 250                 255

Leu Thr Gly Arg Leu Asp Glu Val Leu Arg Thr Leu Val Thr Ser Cys
        260                 265                 270

Phe Leu Val Glu Lys Gln Pro Pro Gln Val Leu Lys Thr Gln Thr Lys
    275                 280                 285

Phe Gln Ala Gly Val Arg Phe Leu Leu Gly Leu Arg Phe Leu Gly Ala
        290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
```

-continued

```
                325                 330                 335
Thr Gly Glu Ile Ile Asn Asn Thr Val Pro Leu Glu Asn Ser Ile Pro
            340                 345                 350
Gly Asn Cys Cys Ser Ala Leu Phe Lys Asn Leu Leu Leu Lys Lys Ile
            355                 360                 365
Lys Arg Cys Glu Arg Lys Gly Thr Glu Ser Val Thr Glu Glu Lys Cys
            370                 375                 380
Ala Val Leu Phe Ser Ala Ser Phe Thr Leu Gly Pro Gly Lys Leu Pro
385                 390                 395                 400
Ile Gln Leu Gln Ala Leu Ser Leu Pro Leu Val Val Ile Val His Gly
            405                 410                 415
Asn Gln Asp Asn Asn Ala Lys Ala Thr Ile Leu Trp Asp Asn Ala Phe
            420                 425                 430
Ser Glu Met Asp Arg Val Pro Phe Val Val Ala Glu Arg Val Pro Trp
            435                 440                 445
Glu Lys Met Cys Glu Thr Leu Asn Leu Lys Phe Met Ala Glu Val Gly
            450                 455                 460
Thr Asn Arg Gly Leu Leu Pro Glu His Phe Leu Phe Leu Ala Gln Lys
465                 470                 475                 480
Ile Phe Asn Asp Asn Ser Leu Ser Met Glu Ala Phe Gln His Arg Ser
            485                 490                 495
Val Ser Trp Ser Gln Phe Asn Lys Glu Ile Leu Leu Gly Arg Gly Phe
            500                 505                 510
Thr Phe Trp Gln Trp Phe Asp Gly Val Leu Asp Leu Thr Lys Arg Cys
            515                 520                 525
Leu Arg Ser Tyr Trp Ser Asp Arg Leu Ile Ile Gly Phe Ile Ser Lys
            530                 535                 540
Gln Tyr Val Thr Ser Leu Leu Leu Asn Glu Pro Asp Gly Thr Phe Leu
545                 550                 555                 560
Leu Arg Phe Ser Asp Ser Glu Ile Gly Gly Ile Thr Ile Ala His Val
            565                 570                 575
Ile Arg Gly Gln Asp Gly Ser Pro Gln Ile Glu Asn Ile Gln Pro Phe
            580                 585                 590
Ser Ala Lys Asp Leu Ser Ile Arg Ser Leu Gly Asp Arg Ile Arg Asp
            595                 600                 605
Leu Ala Gln Leu Lys Asn Leu Tyr Pro Lys Lys Pro Lys Asp Glu Ala
            610                 615                 620
Phe Arg Ser His Tyr Lys Pro Glu Gln Met Gly Lys Asp Gly Arg Gly
625                 630                 635                 640
Tyr Val Pro Ala Thr Ile Lys Met Thr Val Glu Arg Asp Gln Pro Leu
            645                 650                 655
Pro Thr Pro Glu Leu Gln Met Pro Thr Met Val Pro Ser Tyr Asp Leu
            660                 665                 670
Gly Met Ala Pro Asp Ser Ser Met Ser Met Gln Leu Gly Pro Asp Met
            675                 680                 685
Val Pro Gln Val Tyr Pro Pro His Ser His Ser Ile Pro Pro Tyr Gln
            690                 695                 700
Gly Leu Ser Pro Glu Glu Ser Val Asn Val Leu Ser Ala Phe Gln Glu
705                 710                 715                 720
Pro His Leu Gln Met Pro Pro Ser Leu Gly Gln Met Ser Leu Pro Phe
            725                 730                 735
Asp Gln Pro His Pro Gln Gly Leu Leu Pro Cys Gln Pro Gln Glu His
            740                 745                 750
```

```
                    -continued

Ala Val Ser Ser Pro Asp Pro Leu Leu Cys Ser Asp Val Thr Met Val
        755             760             765

Glu Asp Ser Cys Leu Ser Gln Pro Val Thr Ala Phe Pro Gln Gly Thr
    770             775             780

Trp Ile Gly Glu Asp Ile Phe Pro Pro Leu Leu Pro Pro Thr Glu Gln
785             790             795                 800

Asp Leu Thr Lys Leu Leu Leu Glu Gly Gln Gly Glu Ser Gly Gly Gly
            805             810             815

Ser Leu Gly Ala Gln Pro Leu Leu Gln Pro Ser His Tyr Gly Gln Ser
            820             825             830

Gly Ile Ser Met Ser His Met Asp Leu Arg Ala Asn Pro Ser Trp
        835             840             845
```

COMPOSITIONS AND METHODS FOR TREATING STAT-6 ASSOCIATED DISEASES OR CONDITIONS

This application claims the benefit of priority from PCT/US2005/032948, filed Sep. 12, 2005 and U.S. provisional patent application Ser. No. 60/609,884, filed Sep. 14, 2004, the contents of which are incorporated herein by reference in their entireties.

BACKGROUND OF THE INVENTION

Asthma and rhinitis are atopic (allergic) diseases affecting between 20-30% of the population. They are associated with acute and chronic inflammatory responses resulting from contact with protein particles in the environment. Initially, exposure of the airway immune system to otherwise innocuous aeroallergens elicits specific immune responses leading ultimately to production of IgE in predisposed individuals (Togias (2003) *J. Allergy Clin. Immunol.* 111:1171-1183; Braunstahl and Hellings (2003) *Curr. Opin. Pulm. Med.* 9:45-51). Subsequent cross-linking of IgE by these allergens is implicated in acute allergic rhinitis and asthma exacerbations. In those predisposed individuals, allergen exposure results in activation of antigen-specific CD4$^+$ T lymphocytes of the Th2 phenotype; secretion of specific cytokines, including IL-4, IL-5, and IL-13; production of IgE; priming of mast cells; and the recruitment of eosinophils (Wills-Karp (1999) *Annu. Rev. Immunol.* 17:255-281). Th2 cells regulate immune responses by releasing these cytokine mediators into the local environment and via direct cell-cell interactions (Agnello, et al. (2003) *J. Clin. Immunol.* 23:147-161; Leigh, et al. (2004) *Am. J. Respir. Crit. Care Med.* 169:860-867; Bochner and Busse (2004) *J. Allergy Clin. Immunol.* 113:868-875).

Experimental animal models of allergen-induced asthma, in which the profile of cytokines present in the airways can be manipulated, support a role for Th2 cytokines in asthma pathogenesis (see, e.g., Cohn, et al. (1998) *J. Immunol.* 161:3813-3816; Hogan, et al. (1998) *J. Immunol.* 161:1501-1509; Kuperman, et al. (1998) *J. Exp. Med.* 187:939-948; Wills-Karp, et al. (1998) *Science* 282:2258-2261). In murine models of experimental asthma, Th2 cytokines promote airway inflammation and eosinophilia, mucus production, and airway hyperresponsiveness. Taking into account differences in genetic backgrounds and redundancy in cytokine function there is general agreement regarding the role of IL-4, IL-5 and IL-13 in asthma pathogenesis (Wills-Karp (1999) supra; Foster, et al. (2002) *Pharmacol. Ther.* 94:253-264). IL-4 is primarily responsible for the development of CD4$^+$ T cells with a Th2 phenotype (Kopf, et al. (1993) *Nature* 362:245-248; Le Gros, et al. (1990) *J. Exp. Med.* 172:921-929; McKenzie, et al. (1998) *Immunity* 9:423-432). IL-5 is required for eosinophil maturation and activation (Campbell, et al. (1987) *Proc. Natl. Acad. Sci. USA* 84:6629-6633; Clutterbuck, et al. (1987) *Eur. J. Immunol.* 17:1743-1750). IL-13 alone is capable of inducing airway hyperresponsiveness in naïve mice (Wills-Karp, et al. (1998) supra; Grunig, et al. (1998) *Science* 282:2261-2263), even in the complete absence of airway eosinophils (Mattes, et al. (2002) *J. Exp. Med.* 195:1433-1444). Moreover, IL-13 is also implicated in airway remodeling. Stable pulmonary expression of IL-13 induces epithelial cell hypertrophy, mucus cell metaplasia and subepithelial collagen deposition (Zhu, et al. (1999) *J. Clin. Invest.* 103:779-788).

Both IL-4 and IL-13 activate receptors that share the IL-4 receptor alpha (IL-4R alpha) subunit, which induces activation of STAT-6, an SH2 domain containing transcription factor that regulates gene expression (Hou, et al. (1994) *Science* 265:1701-1706; Quelle, et al. (1995) *Mol. Cell. Biol.* 15:3336-3343). Binding of IL-4 or IL-13 to their receptors induces activation of the cytokine receptor associated tyrosine kinases Jak 1, Jak 3 and Tyk 2 (Hershey (2003) *J. Allergy Clin. Immunol.* 111:677-690). These kinases in turn phosphorylate specific tyrosine residues on the IL-4R alpha subunit. Cytoplasmic STAT-6 is recruited to the phosphorylated receptor via the STAT-6 SH2 domain whereupon it is in turn phosphorylated by the receptor associated Jak/Tyk tyrosine kinases. Phosphorylated STAT-6 molecules then dissociate from the receptor, form homodimers via interactions between STAT-6 SH2 domains and phosphotyrosine residues on paired molecules. Only after tyrosine phosphorylation and homodimerization can STAT-6 translocate to the nucleus and regulate IL-4/IL-13-dependent gene expression. Following sensitization and challenge with allergen, STAT-6 knockout mice do not develop the characteristic airway hyperresponsiveness and lung pathology associated with asthma (Kuperman, et al. (1998) supra; Akimoto, et al. (1998) *J. Exp. Med.* 187:1537-1542). Recent data from murine models of experimental asthma suggest that the inability of STAT-6 knockout mice to develop asthma pathogenesis may be due to the loss of IL-13 activity (Wills-Karp, et al. (1998) supra; Grunig, et al. (1998) supra; Mattes, et al. (2001) *J. Immunol.* 167:1683-1692; Walter, et al. (2001) *J. Immunol.* 167:4668-4675; Pope, et al. (2001) *J. Allergy Clin. Immunol.* 108:594-601; Kuperman, et al. (2002) *Nat. Med.* 8:885-889; U.S. Pat. No. 5,866,760) although IL-4-mediated effects may also play a role.

Th2 cytokines, their receptors, and the transcription factors that mediate Th2 cytokine-specific cellular responses are therapeutic targets for the treatment of allergic rhinitis and asthma. One therapeutic approach that has shown promise is to inhibit expression of the proteins that regulate asthma pathogenesis. In experimental asthma, inhibiting expression of IL-4, or the common beta chain shared by IL-5, IL-3 and GM-CSF receptors, or the Th2-specific GATA-3 transcription factor using antisense oligonucleotides effectively inhibits airway inflammatory responses as well as airway hyperresponsiveness in experimental asthma (Allakhverdi, et al. (2002) *Am. J. Respir. Crit. Care Med.* 165:1015-1021; Finotto, et al. (2001) *J. Exp. Med.* 193:1247-1260; Molet, et al. (1999) *J. Allergy Clin. Immunol.* 104:205-214). Further, the inhibition of STAT-6 expression using antisense oligonucleotides is taught in WO 98/40478.

In addition to antisense technology, soluble cytokine receptor subunits have been used to bind to and sequester IL-4 or IL-13 to inhibit allergic asthma (Wills-Karp, et al. (1998) supra; Grunig, et al. (1998) surpa; Henderson, et al. (2000) *J. Immunol.* 164:1086-1095; Borish, et al. (2001) *J. Allergy Clin. Immunol.* 107:963-970). In addition, dominant negative mutants of IL-4 and IL-13 effectively inhibit activation of IL-4/IL-13 receptors by the wild-type cytokines and thus may also have therapeutic potential (Oshima and Puri (2001) *FASEB J.* 15:1469-1471; Hahn, et al. (2003) *J. Allergy Clin. Immunol.* 111:1361-1369). Likewise, deletion mutants of STAT-6 have been generated which are attenuated or function as dominant negative variants which decrease STAT-6 dimerization (U.S. Pat. No. 6,368,828).

A peptide composed of the protein transduction domain from antennapedia coupled to the sequence surrounding tyrosine residue 606 (Tyr-606) of the human IL-4R alpha subunit has also been produced (Stolzenberger, et al. (2001) *Eur. J. Biochem.* 268:4809-4814). This peptide inhibits IL-4-induced tyrosine phosphorylation of STAT-6, although the effect is only transient. Moreover, in vivo activity of this peptide was not disclosed.

Methods for identifying agents which modulate the interaction between STAT-6 and its receptor are taught in U.S. Pat. No. 6,207,391. Agents are identified in competitive binding assays with high affinity receptor peptides of the sequence Tyr-$Xaa_1$-$Xaa_2$-$Xaa_3$ (SEQ ID NO:1), wherein $Xaa_1$ is Lys, Val, Arg, Ile, or Met; $Xaa_2$ is Pro, Ala, or Ser; $Xaa_3$ is Trp, Tyr, Phe, His, or Leu; and the N-terminal tyrosine is phosphorylated.

Further, WO 01/83517 teaches dipeptide derivatives which bind STAT-6 for use as immunomodulators, U.S. Pat. No. 6,426,331 teaches small molecules which modulate the function of STAT proteins, and WO 02/038107 discloses additional compounds for modulating STAT-6 signaling.

SUMMARY OF THE INVENTION

The present invention relates to an isolated chimeric STAT-6 peptide composed of a portion of STAT-6 operably linked to a protein transduction moiety. In one embodiment, the portion of STAT-6 is composed of at least four amino acids residues, wherein said amino acid residues are Tyr-Val-Ser-Thr (SEQ ID NO:2) or Tyr-Val-Pro-Ala (SEQ ID NO:3) wherein the Tyr is phosphorylated. In another embodiment, the portion of STAT-6 is represented by SEQ ID NO:4 or SEQ ID NO:5.

Having demonstrated an in vivo utility for the chimeric STAT-6 peptide in animal models of asthma and combined allergic rhinitis and asthma, the present invention further relates to a method for treating a STAT-6 associated disease or condition. The method involves administering an effective amount of the isolated chimeric STAT-6 peptide of the present invention to a subject having or at risk of having a STAT-6 associated disease or condition so that said disease or condition is treated.

DETAILED DESCRIPTION OF THE INVENTION

The ability of the STAT family of transcription factors to dimerize and translocate to the nucleus where they regulate gene expression is dependent upon SH2 domain binding to phosphotyrosine residues on paired molecules (Calo, et al. (2003) *J. Cell Physiol.* 197:157-168). Thus, activation of STAT-6 depends first on IL-4- or IL-13-induced phosphorylation of Tyr-641 located in the carboxyl terminus of STAT-6 (Hershey (2003) supra). The binding specificity of SH2 domain-containing proteins, including those of the STAT family, is highly selective and is determined primarily by the three amino acids located C-terminal to the phosphorylated tyrosine residue (Heim, et al. (1995) *Science.* 267:1347-1349; Songyang, et al. (1993) *Cell* 72:767-778). Thus, a small peptide composed of the amino acid residues surrounding phosphorylated Tyr-641 of STAT-6 has now been constructed to bind to and inhibit tyrosine phosphorylation and/or dimerization and nuclear translocation of wild-type STAT-6 in IL-4/IL-13 responsive cells. A representative STAT-6 peptide (Gly-Arg-Gly-Tyr*-Val-Ser-Thr-Thr) containing a phosphorylated Tyr is presented herein as SEQ ID NO:4. Because STAT-6 is located intracellularly, the STAT-6 peptide was fused to a derivative of the protein transduction domain from HIV-1 Tat (PTD4; Tyr-Ala-Arg-Ala-Ala-Ala-Arg-Gln-Ala-Arg-Ala; SEQ ID NO:6). The PTD4 domain efficiently enters into cells both in vitro and in vivo (Ho, et al. (2001) *Cancer Res.* 61:474-477) and was used to facilitate transport of the STAT-6 peptide into target cells so that the STAT-6 sequences could bind to and inhibit the wild-type STAT-6 protein in the target cells.

The ability of the PTD4 protein transduction domain to enter cells was confirmed by incubating murine splenocytes with FITC-conjugated PTD4 peptide (FITC-PTD4). Splenocytes were incubated with FITC-PTD4 for various times (30 minutes to 24 hours), subsequently washed and incubated with trypsin to remove surface bound peptide, and analyzed by flow cytometry. Data was normalized to 100%. Half-maximal peptide uptake occurred at 1 hour and plateaued after 4-6 hours (Table 1).

TABLE 1

| Time (Hours) | Percent Maximum (±SEM) |
|---|---|
| 0 | 4.16 ± 0.53 |
| 0.5 | 31.2 ± 4.35 |
| 1.0 | 46.57 ± 6.63 |
| 2.0 | 69.70 ± 8.60 |
| 4.0 | 72.86 ± 8.51 |
| 6.0 | 76.71 ± 7.58 |
| 24.0 | 78.49 ± 14.11 |

To determine the half-life of the intracellular PTD4 peptide in the absence of further uptake, splenocytes were incubated with the FITC-PTD4 peptide for 4 hours, washed and trypsinized, and placed back into complete medium after which intracellular localization of the peptide was monitored over time by flow cytometry. Under these conditions, intracellular FITC-PTD4 had a half-life of approximately four hours, although the peptide was detectable in the splenocytes for up to 24 hours. To monitor stability of the murine-specific PTD4-STAT-6 peptide (STAT-6-IP; Tyr-Ala-Arg-Ala-Ala-Ala-Arg-Gln-Ala-Arg-Ala-Gly-Arg-Gly-Tyr*-Val-Ser-Thr-Thr; SEQ ID NO:7) in murine splenocytes, cells were incubated with the STAT-6-IP for four hours, after which they were washed and trypsinized. The presence of intracellular STAT-6-IP was monitored by western blot analysis of cell lysates harvested at different time points and resolved by SDS-PAGE. The STAT-6-IP was visualized using anti-phosphoSTAT-6 antibody and data normalized to 100% (Table 2). Intracellular STAT-6-IP had a half-life of approximately 8 hours and, similar to the FITC-PTD4 peptide, remained in the cells for up to 24 hours. Together these data demonstrate that the PTD4 protein transduction domain entered cells and facilitated intracellular uptake of the STAT-6-IP.

TABLE 2

| Time (Hours) | Percent Maximum (±STD) |
|---|---|
| 0.5 | 100.00 ± 0.00 |
| 1.0 | 93.69 ± 17.14 |
| 4.0 | 68.33 ± 17.42 |
| 6.0 | 66.56 ± 15.04 |
| 8.0 | 46.47 ± 15.98 |
| 24.0 | 38.50 ± 51.74 |

Subsequently, it was demonstrated that treatment of splenocytes from ovalbumin-sensitized mice with the STAT-6-IP could inhibit STAT-6 and thus decrease ovalbumin-induced production of Th2 cytokines. Splenocytes from ovalbumin-sensitized mice were cultured for four days with no antigen, with ovalbumin alone, or with ovalbumin plus the STAT-6-IP or a STAT-6 Tyr-641 mutant (STAT-6-CP; Tyr-Ala-Arg-Ala-Ala-Ala-Arg-Gln-Ala-Arg-Ala-Gly-Arg-Gly-Phe-Val-Ser-Thr-Thr; SEQ ID NO:8). The STAT-6-IP and STAT-6-CP were added to splenocyte cultures daily. Treatment with the STAT-6-IP, but not the STAT-6-CP, reduced the supernatant levels of both IL-4 and IL-13 (Table 3). Significantly, neither peptide inhibited ovalbumin-induced IFN-gamma production (Table 3), indicating that the STAT-6-IP specifically inhibited STAT-6-dependent activity and not that of STAT-4.

TABLE 3

| Treatment | IL-4 (pg/mL ± SEM) | IL-13 (pg/mL ± SEM) | IFN-gamma (pg/mL ± SEM) |
|---|---|---|---|
| None | 19.8 ± 15.9 | 437.8 ± 224.0 | 50.8 ± 20.2 |
| Ovalbumin | 309.3 ± 49.6 | 2585.4 ± 165.7 | 567.9 ± 93.1 |
| Ovalbumin + STAT-6-IP | 111.6 ± 22.7* | 1630.3 ± 171.4* | 503.4 ± 155.1 |
| Ovalbumin + STAT-6-CP | 212.9 ± 4.1# | 2136.2 ± 94.7# | 513.6 ± 118.3 |

Values represent the mean of three independent experiments ± SEM.
IL-4, $F_{(3,11)} = 19.3$, p = 0.001. IL-13, $F_{(3,19)} = 29.58$, p < 0.0001. IFN-gamma, $F_{(3,11)} = 4.90$, p = 0.032.
*p = 0.005 compared to cells cultured with ovalbumin.
p > 0.05 compared to cells cultured with ovalbumin.

The levels of mRNA encoding IL-4, IL-13 and IFN-gamma were also evaluated by semiquantitative RT-PCR analysis. Ovalbumin-induced expression of both IL-4 and IL-13 mRNA was inhibited in splenocytes cultured with the STAT-6-IP and not the STAT-6-CP. On the other hand, expression of IFN-gamma mRNA did not change in splenocytes, whether cultured with ovalbumin or ovalbumin plus the STAT-6-IP or control STAT-6-CP. The number of CD4+ T cells producing IL-4 was also quantified by intracellular cytokine staining. When splenocytes from ovalbumin-sensitized mice were cultured with ovalbumin, there was a significant increase in the number of CD4+ lymphocytes expressing IL-4 (Table 4). The increase in IL-4 expression was abrogated in splenocytes cultured with ovalbumin in the presence of the STAT-6-IP, while the STAT-6-CP had no effect. These data indicate that the STAT-6-IP efficiently entered cells and selectively inhibited Th2 cytokine production, leaving Th1 cytokine production intact.

TABLE 4

| Treatment | Percentage of IL4 positive cells ± SEM |
|---|---|
| None | 44.96 ± 11.05 |
| Ovalbumin | 90.21 ± 8.02 |
| Ovalbumin + STAT-6-IP | 36.01 ± 7.85* |
| Ovalbumin + STAT-6-CP | 92.13 ± 5.62# |

Values represent the mean of three independent experiments ± SEM.
$F_{(3,11)} = 12.46$, p = 0.002.
*p = 0.008 compared to cells cultured with ovalbumin.
p = 0.99 not significant compared to cells cultured with ovalbumin.

Using a murine model of experimental asthma, wherein mice are sensitized to allergen intraperitoneally (i.p.), as well as a murine model of combined allergic rhinitis and asthma, that was designed to mimic events that occur in the development of human atopy (McCusker, et al. (2002) *J. Allergy Clin. Immunol.* 110:891-898), it was demonstrated that the STAT-6-IP peptide could inhibit Th2-dependent allergic airways disease in vivo. In the combined allergic rhinitis and asthma model, non-anaesthetized mice are locally sensitized with ovalbumin intranasally (i.n.), the primary route of allergen exposure in man (McCusker, et al. (2002) supra). Normal saline was used as a control. In both models sensitized mice produce ovalbumin-specific IgE and upon i.n. ovalbumin challenge, develop inflammation and eosinophilia in both the upper and lower airways as well as IL-13-dependent airway hyperresponsiveness (McCusker, et al. (2002) supra; Wang and McCusker (2005) *Clin. Exp. Allergy* 35(8):1104-11). Thus, in each model of allergic airway disease, the STAT-6-IP or control STAT-6-CP was given locally, i.n., to non-anaesthetized, ovalbumin-sensitized mice prior to each of five daily allergen challenges. Consistent with its ability to inhibit STAT-6-dependent activity in vitro, the STAT-6-IP inhibited allergen-induced accumulation of granulocytes in the lung, quantified in bronchoalveolar lavage (BAL) fluid, independent of the site of sensitization (Table 5).

TABLE 5

| Sensitization Treatment | Challenge | Granulocytes/100 counted from BAL (±SEM) |
|---|---|---|
| Normal Saline | Normal Saline | 5.22 (±0.26) |
| i.n. Ovalbumin | Ovalbumin | 26.73 (±0.80) |
| i.p. Ovalbumin | Ovalbumin | 37.57 (±0.32) |
| i.n. Ovalbumin + STAT-6-IP | Ovalbumin | 12.57 (±0.54)* |
| i.n. Ovalbumin + STAT-6-CP | Ovalbumin | 22.27 (±0.60)# |
| i.p. Ovalbumin + STAT-6-IP | Ovalbumin | 19.63 (±0.97)** |
| i.p. Ovalbumin + STAT-6-CP | Ovalbumin | 34.75 (±0.68)# |

Experiments were carried out with 50 microgram STAT-6-IP or STAT-6-CP. $F_{(6,34)} = 75.04$, p = 0.0005.
*Compared with local ovalbumin, p = 0.0005.
**Compared with systemic ovalbumin, p = 0.0005.
No significant difference when compared with respective ovalbumin positive control groups.

STAT-6-IP also decreased the ovalbumin-induced increase of IL-13 in the BAL fluid (Table 6) and the highest dose of STAT-6-IP inhibited IL-13 to baseline levels.

TABLE 6

| Sensitization Treatment | Challenge | IL-13, pg/mL (±SEM) |
|---|---|---|
| Normal Saline | Normal Saline | 55.67 (±6.34) |
| Ovalbumin | Ovalbumin | 84.95 (±5.15) |
| Ovalbumin + STAT-6-CP (150 μg) | Ovalbumin | 75.75 (±5.60) |
| Ovalbumin + STAT-6-IP (15 μg) | Ovalbumin | 63.60 (±12.11) |
| Ovalbumin + STAT-6-IP (50 μg) | Ovalbumin | 39.55 (±7.18)# |
| Ovalbumin + STAT-6-IP (150 μg) | Ovalbumin | 33.55 (±1.02)*## |

Experiments were carried out with the indicated amounts of STAT-6-IP or STAT-6-CP. For group comparison overall effect was significant. $F_{(5,21)} = 7.31$, p = 0.001.
Compared with ovalbumin, #p = 0.008, ##p = 0.001.
Compared with normal saline, *p > 0.05, not significant.

Histology of lungs revealed that the ovalbumin-induced lung inflammation, including airway eosinophilia, was reduced in animals treated with the STAT-6-IP, while lung inflammation in mice that received the STAT-6-CP did not differ from that in ovalbumin-sensitized and -challenged animals. Further, airway hyperresponsiveness, a hallmark of asthma, was also inhibited by the STAT-6-IP in mice sensitized either systemically or locally (Table 7).

TABLE 7

| Sensitization Treatment | Challenge | Response Rmax (cm H$_2$O x s/mL ± SEM) |
|---|---|---|
| Normal Saline | Normal Saline | 1.19 ± 0.07 |
| i.n. Ovalbumin | Ovalbumin | 1.92 ± 0.08 |
| i.p. Ovalbumin | Ovalbumin | 1.87 ± 0.06 |
| i.n. Ovalbumin + STAT-6-IP | Ovalbumin | 1.57 ± 0.06*# |
| i.n. Ovalbumin + STAT-6-CP | Ovalbumin | 1.80 ± 0.07 |
| i.p. Ovalbumin + STAT-6-IP | Ovalbumin | 1.44 ± 0.09** |
| i.p. Ovalbumin + STAT-6-CP | Ovalbumin | 1.85 ± 0.06 |

Experiments were carried out with 50 microgram STAT-6-IP or STAT-6-CP. Overall comparison, $F_{(6,54)} = 13.45$, p = 0.0005.
*Compared with local ovalbumin, p = 0.027.
**Compared with systemic ovalbumin, p = 0.004.
Compared with normal saline, p = 0.01.

Significantly, the STAT-6-IP inhibited the accumulation of granulocytes and IL-13 in the BAL (Table 6 and Table 8), as well as airway hyperresponsiveness (Table 9), in a dose-dependent manner.

TABLE 8

| Sensitization Treatment | Challenge | Granulocytes/100 counted from BAL (±SEM) |
|---|---|---|
| Normal Saline | Normal Saline | 5.00 ± 0.67 |
| Ovalbumin | Ovalbumin | 22.33 ± 1.47 |
| Ovalbumin + STAT-6-CP (150 µg) | Ovalbumin | 21.42 ± 1.56 |
| Ovalbumin + STAT-6-IP (15 µg) | Ovalbumin | 24.00 ± 0.52 |
| Ovalbumin + STAT-6-IP (50 µg) | Ovalbumin | 13.72 ± 1.38* |
| Ovalbumin + STAT-6-IP (150 µg) | Ovalbumin | 10.71 ± 0.80* |

Experiments were carried out with the indicated amounts of STAT-6-IP or STAT-6-CP. For group comparison overall effect was significant. $F_{(5,22)} = 46.92$, $p = 0.0005$.
Compared with ovalbumin, *p = 0.0005.

TABLE 9

| Sensitization Treatment | Challenge | Response Rmax (cm H$_2$O × s/mL ± SEM) |
|---|---|---|
| Normal Saline | Normal Saline | 1.41 (±0.04) |
| Ovalbumin | Ovalbumin | 2.02 (±0.17)# |
| Ovalbumin + STAT-6-CP (150 µg) | Ovalbumin | 2.53 (±0.31)## |
| Ovalbumin + STAT-6-IP (15 µg) | Ovalbumin | 1.65 (±0.08) |
| Ovalbumin + STAT-6-IP (50 µg) | Ovalbumin | 1.50 (±0.10)* |
| Ovalbumin + STAT-6-IP (150 µg) | Ovalbumin | 1.37 (±0.04)** |

Experiments were carried out with the indicated amounts of STAT-6-IP or STAT-6-CP. For group comparison overall effect was significant. $F_{(5,45)} = 10.61$, $p = 0.0005$.
Compared with normal saline, p = 0.02.
not significant compared with ovalbumin, p = 0.11.
*Compared with ovalbumin, p = 0.049.
**Compared with ovalbumin, p = 0.014.

Although this exemplified STAT-6 chimeric peptide had potent inhibitory activity in vitro and in vivo, it did not appear to inhibit Tyr phosphorylation of STAT-6 to any significant degree. Not to be bound by theory, it is contemplated that this exemplary STAT-6 chimeric peptide blocked STAT-6 activity by interfering with the dimerization of STAT-6 monomers that is required before the STAT-6 dimer can translocate to the nucleus, bind to the STAT-6-dependent genes and initiate transcription. However, it is contemplated that other chimeric STAT-6 peptides can be produced which also, or alternatively, inhibit tyrosine phosphorylation. In addition to the treatment of allergic rhinitis or asthma, the peptides disclosed herein will also be useful in treating (i.e., suppressing or inhibiting) the full spectrum of immune disorders which require transcriptional activation by STAT-6 dimer, including allergic conditions (e.g., atopic dermatitis, contact dermatitis, anaphylaxis, food or drug induced allergy, conjunctivitis, uveitis, hypersensitivity reactions, alveolitis and psoriasis), Churg-Strauss syndrome, delayed-type hypersensitivity, urticaria, angiodema, eczema, scleroderma, and systemic lupus erythematosus.

Thus, the present invention relates to a chimeric STAT-6 peptide containing a portion of STAT-6 and a protein transduction moiety. A portion of STAT-6 is intended to mean a peptide composed of at least Tyr-641 and the three amino acid residues immediately C-terminal to Tyr-641 of the native STAT-6 protein sequence, wherein Tyr-641 is phosphorylated (*). Exemplary portions of STAT-6 include amino acid residues Tyr*-Val-Ser-Thr (SEQ ID NO:2) of murine STAT-6 (GENBANK Accession No. P52633) and amino acid residues Tyr*-Val-Pro-Ala (SEQ ID NO:3) of human STAT-6 (GENBANK Accession No. NP_003144). While the portion of STAT-6 contains Tyr-641 and the three amino acid residues immediately C-terminal to Tyr-641, the portion of STAT-6 can further contain additional amino acid residues on the C-terminus, N-terminus, or C- and N-terminus. For example, SEQ ID NO:4 (Gly-Arg-Gly-Tyr*-Val-Ser-Thr-Thr) and SEQ ID NO:5 (Gly-Arg-Gly-Tyr*-Val-Pro-Ala-Thr) contain one additional amino acid residue on the C-terminal end and three additional amino acid residues on the N-terminal end. While it is contemplated that a portion of STAT-6 protein can include all or nearly all amino acid residues encoding a dominant negative STAT-6 protein (e.g. lacking the transactivation domain), for ease of synthesis and delivery, it is desirable that the portion of STAT-6 is generally about 40, 30, 20, 10, 9, 8, 7, 6, 5 or 4 amino acids in length. In one embodiment, a portion of a STAT-6 protein containing Tyr-641 is four amino acids in length. In another embodiment, a portion of a STAT-6 protein is eight amino acids in length and contains at least Tyr-641 and the three amino acid residues immediately C-terminal to Tyr-641. Exemplary STAT-6 peptides are represented by SEQ ID NO:2, SEQ ID NO:3, SEQ ID NO:4 and SEQ ID NO:5.

As will be appreciated by one of skill in the art, variants of a portion of a STAT-6 peptide can also be used to bind to and inhibit the activity of STAT-6. Such variants generally contain Tyr-641 and the three amino acid residues immediately C-terminal to Tyr-641 which are found in the native STAT-6 protein sequence; however when additional amino acid residues are added to the C- or N-terminus, said addition amino acid residues can be identical to those found in the native STAT-6 protein sequence or can be variants of the STAT-6 peptide sequence. Such variants can be conserved or non-conserved amino acid changes which do not significantly affect the binding specificity of Tyr-641 and the three amino acid residues immediately C-terminal to Tyr-641. For example, in making amino acid substitutions, the hydropathic index of amino acids may be considered. The importance of the hydropathic amino acid index in conferring interactive biologic function on a protein is generally understood in the art (see, Kyte and Doolittle (1982) *J. Mol. Biol.* 157:105). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is also understood in the art that the substitution of amino acids can be made on the basis of hydrophilicity. U.S. Pat. No. 4,554,101 teaches that the greatest local average hydrophilicity of a protein, as governed by the hydrophilicity of its adjacent amino acids, correlates with a biological property of the protein.

As used herein, a protein transduction moiety is any molecule which can be operably attached to the STAT-6 peptide to facilitate, enhance, or increase the intracellular transport or delivery of STAT-6 into a cell. Such a moiety can be a protein, peptide or small molecule. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245:1-7), a polylysine peptide containing Tat PTD (Hashida, et al. (2004) *Br. J. Cancer* 90(6):1252-8), Pep-1 (Deshayes, et al. (2004) Biochemistry 43(6):1449-57) or an HSP70 protein or fragment thereof (WO 00/31113) is suitable for delivering a STAT-6 peptide into the cell. Not to be bound by theory, it is believed that such transport domains are highly basic and appear to interact strongly with the plasma membrane and subsequently enter cells via endocytosis (Wadia, et al. (2004) *Nat. Med.* 10:310-315). Animal model studies indicate that chimeric proteins containing a protein transduction domain fused to a full-length protein or inhibitory peptide can protect against ischemic brain injury and neuronal apoptosis; attenuate hypertension; prevent acute inflammatory responses; and regulate long-term spatial memory responses (Blum and Dash (2004) *Learn. Mem.* 11:239-243; May, et al. (2000) *Science* 289:1550-1554; Rey, et al. (2001) *Circ. Res.* 89:408-414; Denicourt and Dowdy (2003) *Trends Pharmacol. Sci.* 24:216-218; Myou, et al. (2003) *J. Exp. Med.* 198(10):1573-82; Myou, et al. (2003) *J. Immunol.* 171(8):4379-84).

Exemplary peptide-based protein transduction moieties are presented in Table 10.

TABLE 10

| SOURCE | AMINO ACID SEQUENCE | SEQ ID NO: |
|---|---|---|
| PTD-4[a] | YARAAARQARA | 6 |
| HIV TAT[a] | YGRKKRRQRRR | 9 |
| PTD-3[a] | YARKARRQARR | 10 |
| PTD-5[a] | YARAARRAARR | 11 |
| PTD-6[a] | YARAARRAARA | 12 |
| PTD-7[a] | YARRRRRRRRR | 13 |
| ANTp[b] | RQIKIWFQNRRMKWKK | 14 |
| Transportin[b] | GWTLNSAGYLLGKINLKALAALAKKIL | 15 |

[a]Ho, et al. (2001) *Cancer Res.* 61: 474-477.
[b]Schwartz and Zhang (2000) *Curr. Opin. Mol. Ther.* 2: 2.

Suitable small molecule protein transduction moieties which can be linked to STAT-6 peptides include, but are not limited to, nonpeptidic polyguanidylated dendritic structures (Chung, et al. (2004) *Biopolymers* 76(1):83-96) or poly[N-(2-hydroxypropyl) methacrylamide] (Christie, et al. (2004) *Biomed. Sci. Instrum.* 40:136-41).

The STAT-6 peptide and protein transduction domain can be operably joined or linked by non-biodegradable or biodegradable bonds. A non-biodegradable bond is defined as a bond which is relatively stable in both biological fluids, such as blood or plasma, and the intracellular environment. A biodegradable bond is defined as a bond which is relatively stable in biological fluids but is easily broken inside a cell to release the STAT-6 peptide from the protein transduction domain. An exemplary biodegradable linkage is a disulfide bond; nearly all the cysteine residues in circulating (blood) proteins are in the oxidized (disulfide) form whereas virtually all cysteine residues in intracellular proteins are reduced. Therefore, a disulfide bond between two moieties will remain appreciably intact while in transit, and subsequently cleaved to release the two moieties upon exposure to the intracellular environment. See, for example, U.S. Pat. No. 6,258,774 and Huang, et al. ((1998) *Bioconjugate Chem.* 9:612-617) for details on disulfide biodegradable bonds and Robbins, et al. ((2002) *Biotechniques* 33(1):190-2, 194) which teach delivery of a prototype cargo peptide by a hepta-arginine protein transduction moiety linked via a releasable disulfide linkage. An ester bond is another suitable biodegradable bond for operably linking a STAT-6 peptide to a protein transduction moiety. Further, pH sensitive bonds can be used (see, e.g., Christie, et al. (2004) supra). For example, a spacer can be introduced which is stable under physiological conditions (pH 7.4) and hydrolytically degradable in mild acidic environment (e.g., endosomes; pH approximately 5).

Conversely, non-biodegradable bonds include all other bonds for joining two molecules together that are not degradable, for example, single, double and triple carbon-carbon bonds; amide bonds; secondary amine linkages; thioether bonds; ether bonds; and thiocarbamate bonds. It will be appreciated by the skilled artisan that the type of bond used will vary with protein transduction moiety selected for attachment to the STAT-6 peptide.

It is contemplated that the protein transduction moiety can be operably linked to the STAT-6 peptide at either the N- or C-terminal end of the STAT-6 peptide. As one of skill in the art can appreciate, the type of linkage selected can vary depending on the orientation of the protein transduction moiety and the STAT-6 peptide and the protein transduction moiety selected (i.e., peptide or non-peptide based).

A chimeric STAT-6 peptide of the invention can be recombinantly-produced or chemically-synthesized. Direct peptide synthesis using solid-phase techniques is well-established in the art (Merrifield J. (1963) *J. Am. Chem. Soc.* 85:2149-2154). Protein synthesis can be performed using manual techniques or by automation. Automated synthesis can be achieved, for example, using Applied Biosystems 431A Peptide Synthesizer (Perkin Elmer, Boston, Mass.).

In general, recombinant production of a chimeric STAT-6 peptide of the invention requires incorporation of nucleic acid sequences encoding a portion of STAT-6 (e.g., a portion of STAT-6 containing Tyr-641) into a recombinant expression vector in a form suitable for expression of the protein in a host cell. When the protein transduction moiety is also peptide-based, the nucleic acid sequences encoding said moiety can also incorporated, either upstream or downstream of the nucleic acid sequences encoding the STAT-6 peptide so that the STAT-6 peptide and protein transduction moiety are translated in-frame.

A suitable form for expression provides that the recombinant expression vector, viral vector, or plasmid includes one or more regulatory sequences operatively-linked to the nucleic acids encoding the chimeric STAT-6 peptide of the invention in a manner which allows for transcription of the nucleic acids into mRNA and translation of the mRNA into the protein. Regulatory sequences can include promoters, enhancers and other expression control elements (e.g., polyadenylation signals). Such regulatory sequences are known to those skilled in the art and are described in Goeddel D. D., ed., Gene Expression Technology, Academic Press, San Diego, Calif. (1991). It should be understood that the design of the vector can depend on such factors as the choice of the host cell to be transfected and/or the level of expression required. Nucleic acid sequences or vectors harboring nucleic acid sequences encoding a polypeptide of the invention can be introduced into a host cell, which can be of eukaryotic or prokaryotic origin, by standard techniques for transforming cells. Suitable methods for transforming host cells can be found in Sambrook, et al. (Molecular Cloning: A Laboratory Manual, 3rd Edition, Cold Spring Harbor Laboratory Press (2000)) and other laboratory manuals. The number of host cells transformed with a nucleic acid sequence encoding a chimeric STAT-6 peptide of the invention will depend, at least in part, upon the type of expression vector used and the type of transformation technique used. Nucleic acids can be introduced into a host cell transiently, or more typically, for long-term expression of a chimeric STAT-6 peptide of the invention, the nucleic acid sequence is stably integrated into the genome of the host cell or remains as a stable episome in the host cell. Once produced, a chimeric STAT-6 peptide of the invention can be recovered from culture medium as a secreted peptide, although it also can be recovered from host cell lysates when directly expressed without a secretory signal. When a chimeric STAT-6 peptide of the invention is expressed in a recombinant cell other than one of human origin, the peptide is substantially free of proteins or polypeptides of human origin. However, it may be necessary to purify the peptide of the invention from recombinant cell proteins using conventional protein purification methods to obtain preparations that are substantially homogeneous as to said peptide. As a first step, the culture medium or lysate is centrifuged to remove particulate cell debris. The recombinant peptide is then purified using any of the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX® G-75; ligand affinity chromatography, and protein A SEPHAROSE® columns to remove contaminants such as IgG.

It is further contemplated that the chimeric STAT-6 peptide of the invention can be synthesized as a peptidomimetic. Peptidomimetics are desirable as therapeutic agents to peptides owing to their enhanced bioavailability and relative lack of attack from proteolytic enzymes. Accordingly, the present invention also relates to peptidomimetics and other analogs or variants of the STAT-6 peptide of the present invention. A potential analog can be examined through the use of computer modeling using a docking program such as GRAM, DOCK, or AUTODOCK. This procedure can include computer fitting of potential analogs. Computer programs also can be employed to estimate the attraction, repulsion, and steric hindrance of an analog to a potential binding site. Generally a tighter fit (e.g., lower steric hindrance, and/or greater attractive force) results in fewer side effects and more potent activity.

Independent of the method by which the chimeric STAT-6 peptide is produced, the STAT-6 peptide is phosphorylated at Tyr-641. Phosphorylation of Tyr-641 can be carried out during chemical synthesis using Boc chemistry or standard Fmoc chemistry (e.g., Fmoc-Tyr[PO(OBzl)OH]—OH) (Wakamiya, et al. (1994) *Chem. Lett.* 1099-1102; Miyoshi, et al. (2000) *Chem. Pharm. Bull.* (*Tokyo*) 48:1230-3; Perich, et al. (1993) *Bioorg. Med. Chem.* 1:381-8; Perich, et al. (1994) *Int. J. Pept. Protein Res.* 43:39-46), in vivo, or by post-phosphorylation of an isolated peptide (Sakaguchi and Roller (1996) *Genetic Engineering* 18:249-279).

As shown herein, a chimeric STAT-6 peptide is useful in treating allergic rhinitis or asthma and is contemplated as being useful in treating other immune disorders which require transcriptional activation by STAT-6 dimer. Therefore, the present invention also relates to a method for treating diseases or conditions associated with STAT-6 activation. The method involves administering a chimeric STAT-6 peptide to a subject having or at risk of having a STAT-6 associated disease or condition. As many of the disease or conditions associated with STAT-6 involve individuals predisposed to an allergen wherein subsequent allergen exposure results in the signal transduction cascade leading to STAT-6 activation, these individuals, while not exhibiting signs or symptoms, would have or be at risk of having a STAT-6 associated disease or condition. Desirably, an effective amount of a chimeric STAT-6 peptide is an amount sufficient to effect beneficial or desired results, including clinical results, and, as such, an effective amount of a chimeric STAT-6 peptide is one which includes, but is not limited to, inhibition, alleviation or amelioration of one or more symptoms or conditions; diminishment of extent of disease; stabilized (i.e., not worsening) state of disease; or delay or slowing of disease progression. Treatment can also mean prolonging survival as compared to expected survival if not receiving treatment. As will be understood by the skilled artisan, the signs or symptoms of the disease or condition can vary with the disease or condition and are generally well-known to the skilled clinician. See, for example, The Merck Manual of Diagnosis and Therapy, Section 6, Pulmonary Disorders and Section 12, Immunology; Allergic Disorders.

For use in the methods of the present invention, the chimeric STAT-6 peptide is conveniently used or administered in a pharmaceutical composition containing the chimeric peptide in combination with a pharmaceutically acceptable carrier or vehicle. Such compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000.

A pharmaceutically acceptable carrier or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in formulations.

Wetting agents, emulsifiers and lubricants, such as sodium lauryl sulfate and magnesium stearate, as well as coloring agents, release agents, coating agents, sweetening, flavoring and perfuming agents, preservatives, flavonoids and antioxidants can also be present in the compositions.

A chimeric STAT-6 peptide, also referred to herein as the active agent, can be administered locally or systemically via any route including, but not limited to, oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration. The most suitable route in any given case will depend on the nature and severity of the condition being treated.

For oral administration, the chimeric STAT-6 peptide can be combined with one or more carriers and used in the form of ingestible tablets, buccal tablets, troches, capsules, elixirs, suspensions, syrups, wafers, chewing gums, foods and the like. Such compositions and preparations should contain at least 0.1% of active agent. The percentage of the active agent and preparations can, of course, be varied and can conveniently be between about 0.1 to about 100% of the weight of a given unit dosage form. The amount of active agent in such compositions is such that an effective dosage level will be obtained.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like.

A syrup or elixir can contain the active agent, sucrose or fructose as a sweetening agent, methyl and propylparabens as preservatives, a dye and flavoring such as cherry or orange flavor. Of course, any material used in preparing any unit dosage form should be substantially non-toxic in the amounts employed. In addition, the active agent can be incorporated into sustained-release preparations and devices including, but not limited to, those relying on osmotic pressures to obtain a desired release profile.

Intraperitoneal injection of beta-galactosidase protein fused to a protein transduction domain results in delivery of the biologically active fusion protein to all tissues in mice (Schwarze, et al. (1999) *Science* 285(5433):1569-72), thus a chimeric STAT-6 peptide of the present invention can likewise be administered by injection. Pharmaceutical compositions of the present invention suitable for parenteral administration contain sterile aqueous and non-aqueous injection solutions of the active agent, which preparations are generally isotonic with the blood of the intended recipient. These preparations can contain anti-oxidants, buffers, bacteriostats and solutes which render the composition isotonic with the blood of the intended recipient. Aqueous and non-aqueous sterile suspensions can include suspending agents and thickening agents. The compositions can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Prolonged absorption of an injectable composition can be brought about by including in the composition an agent which delays absorption, for example, monostearate salts and gelatin. The active agent can be prepared with carriers that protect the agent against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such compositions are patented or generally known to those skilled in the art.

In one embodiment, compositions suitable for topical application to the skin can take the form of an ointment, cream, lotion, paste, gel, spray, aerosol, oil or other pharmaceutical formulation which accomplishes direct contact between the active agent and the skin. Topical formulations can also be prepared which are suitable for occlusive therapy.

Formulations in the forms of ointments, creams, lotions and pastes can generally have carriers in the forms of oleaginous bases (e.g., White Petrolatum and White Ointment); absorption bases formed by adding a water-in-oil emulsifying agent to an oleaginous base (e.g., Hydrophilic Petrolatum, AQUABASE®, and AQUAPHOR®); water-in-oil emulsion bases, prepared by adding water to an absorption base (e.g., HYDROCREAM®, EUCERIN®, NIVEA®, and Cold Cream); oil-in-water emulsion bases (e.g., DERMABASE®, UNIBASE®, VELVACHOL®, and hydrophilic ointment); and water soluble bases (e.g., polyethylene glycol ointment such as PEG 400-600 G or PEG 3350-400 G). Suitable carriers to produce a spray, gel, or aerosol are well-known in the art.

A carrier for topical application can also contain additional ingredients such as other carriers, moisturizers, humectants, emollients, dispersants, radiation blocking compounds, cleansing agents, anti-infective agents (e.g., antibiotics, fungicides, scabicides, or pediculicides), anti-inflammatory agents (e.g., corticosteroids), keratolytics (agents that soften, loosen, and facilitate exfoliation of the squamous cells of the epidermis), as well as other suitable materials that do not have a significant adverse effect on the activity of the topical composition. Additional ingredients can include, for example a sodium acid phosphate moisturizer, witch hazel extract, glycerine humectant, apricot kernal oil emollient, or corn oil dispersant. Other materials which can optionally be included in a topical composition include inositol or B-complex vitamins.

Further, a topical composition containing a chimeric STAT-6 peptide of the present invention and a pharmaceutically acceptable carrier can contain transdermal or skin penetrant enhancers. Alternatively, the pharmaceutically acceptable carrier is a skin penetrant enhancer. Suitable skin penetrant enhancers include, but are not limited to, solvents such as water, alcohols (e.g., methanol, ethanol, 2-propanol), alkyl methyl sulfoxides (e.g., dimethylsulfoxide, decylmethyl sulfoxide, tetradecyl methyl sulfoxide), pyrrolidones (e.g., 2-pyrrolidone, N-methyl-2-pyrrolidone, N-(2-hydroxyethyl)pyrrolidone), laurocapram (AZONE®), and other solvents such as acetone, dimethyl acetamide, dimethyl formamide, tetrahydrofurfuryl alcohol; amphiphiles such as anionic surfactants (e.g., docusate sodium, sodium lauryl sulfate), cationic surfactants (e.g., quaternary ammonium salts), amphoteric surfactants (e.g., lecithins, cephalins, alkylbetamines), nonionic surfactants (mono-, di-, and triglycerides), and other fatty acids and alcohols (e.g., lauryl, cetyl, and stearyl alcohols), sucrose, sorbitan and PEG; urea and N,N-dimethyl-m-toluamide.

Compositions suitable for transdermal administration can be presented as discrete patches adapted to remain in intimate contact with the epidermis of the recipient for a prolonged period of time. There are two basic designs of the patch system that dictate release characteristics of the active agent and patch behavior: (i) matrix or monolithic and (ii) reservoir or membrane. It is contemplated that either patch system is suitable for delivery of an active agent disclosed herein. Compositions suitable for transdermal administration can also be delivered by iontophoresis (see, for example, *Pharmaceutical Research* 3 (6):318 (1986)) and typically take the form of an optionally buffered aqueous solution of the compound.

In another embodiment, the chimeric STAT-6 peptide is formulated for nasal or oral administration to the lungs for the treatment of allergic rhinitis or asthma or other diseases or conditions of the lung. In particular embodiments, the active agent is administered by an aerosol suspension of respirable particles containing the active agent, which the subject inhales. The respirable particles can be liquid or solid. The term aerosol includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn, et al. (1992) *J. Pharmacol. Toxicol. Methods* 27:143-159. Aerosols of liquid particles containing the active agent can be produced by any suitable means, such as with a pressure-driven aerosol nebulizer or an ultrasonic nebulizer, as is known to those of skill in the art. See, e.g., U.S. Pat. No. 4,501,729. Aerosols of solid particles containing the active agent can likewise be produced with any solid particulate medicament aerosol generator, by techniques known in the pharmaceutical art. See, for example U.S. Pat. Nos. 6,169,068 and 6,334,999.

In general, the chimeric STAT-6 peptide is introduced into the subject in an amount between 0.01 mg per kg body weight of the mammal up to about 100 mg per kg body weight of said mammal, or more desirably, in the range of about 1 mg per kg body weight of the mammal to about 50 mg per kg body weight of the mammal. One of ordinary skill in the art may readily determine a volume or weight of pharmaceutical composition to be administered which corresponds to this dosage based on the concentration of chimeric STAT-6 peptide in the pharmaceutical composition. Further, a chimeric STAT-6 peptide of the present invention can be administered once, twice or three times per day or weekly depending on the formulation and the need of the subject being treated.

In other embodiments, the chimeric STAT-6 peptide is administered in combination with another agent such as, for example, anti-IL-9 antibody, loratidine, fluticasone propionate, beclamethasone diproprionate, budesonide, salmeterol xinafoate, ipratropium bromide, fexofenadine hydrochloride, cetirizine dihydrochloride, triamcinolone acetonide, cromolyn, salbutamol, montelukast sodium, ketotifen hydrogen fumarate, formoterol, zafirlukast, momefasone furoate, azelastine hydrochloride, epinastine, seratrodast, captropril, rampril, zofenopril, colchicine, enalapril, lisinopril, trandolapril, gold sodium thiomalate, calcipotriene, cyclosporine, vinblastine or dapsone.

In some cases, when combinations of active agents are used, the amount of each agent administered can be less than the amount required when the agent is used alone. For example, when the agent is synergistic with the chimeric STAT-6 peptides provided herein said agent can be used in an amount that is less than one-half of the normal efficacious dose.

Additionally, when therapy is provided using a combination of agents, the administration of the agents can be simultaneous or sequential. In instances wherein administration is sequential, the agents can be administered in any order and the periods between administration of a first and second agent can be minutes, hours, days, weeks, or months. Dosages of other active agents can be determined by methods known in the art, see, e.g., Remington: The Science and Practice of Pharmacy, Alfonso R. Gennaro, editor, 20th ed. Lippincott Williams & Wilkins: Philadelphia, Pa., 2000.

The selected effective dosage level of the chimeric STAT-6 peptide or the chimeric STAT-6 peptide in combination with another agent will depend upon a variety of factors including the route of administration, the time of administration, the rate of excretion or metabolism of the particular chimeric STAT-6 peptide being employed, the duration of the treatment, other drugs, compounds and/or materials used in combination with the particular active agent employed, the age, sex, weight, condition, general health and prior medical history of the patient being treated, and like factors well-known in the medical arts.

The invention is described in greater detail by the following non-limiting examples.

EXAMPLE 1

Peptide Synthesis and Uptake by Splenocytes

STAT-6 peptides (STAT-6-IP and STAT-6-CP) were synthesized using an automated PE/Biosystems 431A peptide synthesizer and Fmoc/HBTU synthesis chemistry (University of Calgary Integrated Peptide Services, Calgary, Alberta, Canada). The FITC-conjugated PTD4 peptide was synthesized according to standard methods (Sheldon Biotechnology Center, Montreal, Quebec, Canada) Peptides were purified by reversed phase-HPLC and analyzed by mass spectrometry.

To monitor peptide uptake, splenocytes in Dulbecco's Modified Eagle Medium (DMEM)/10% fetal bovine serum (FBS) were incubated continuously with FITC-conjugated PTD4 peptide (100 μM) for 30 minutes to 24 hours. At each time point, surface bound peptide was removed by washing cells twice with phosphate-buffered saline (PBS) and then incubating cells with trypsin for five minutes. Ten thousand cells were subsequently analyzed by flow cytometry. To monitor the half-life of intracellular peptide (in the absence of uptake), splenocytes in DMEM/10% FBS were incubated with FITC-conjugated PTD4 peptide (100 μM) for four hours, after which they were washed twice with PBS and incubated with trypsin for five minutes. Splenocytes were returned to DMEM/10% FBS and intracellular localization of peptide monitored over time by flow cytometry.

To monitor stability of the STAT-6-IP in murine splenocytes, cells in DMEM/10% FBS were incubated with the STAT-6-IP (100 μM) for four hours, after which they were washed twice with PBS and trypsinized. Splenocytes were then incubated with soybean trypsin inhibitor (0.5 mg/mL in 10 mM sodium tetraborate) for 5 minutes. The cells were washed again once in PBS and subsequently placed back into complete medium. At different time points, cells were harvested and lysed in tricine sample buffer (100 mM Tris-HCl, pH 6.8, 24% glycerol, 8% SDS, 200 mM DTT). Lysates were clarified and equal concentrations (20 μg/lane) resolved by SDS-PAGE on 18% tris-tricine gels, after which proteins were transferred to PVDF membrane. For western immunoblot analysis, membranes were blocked for one hour in TBST (10 mM Tris-Cl pH 7.4, 2.5 mM EDTA, 150 mM NaCl, 0.1% TWEEN™-20) containing 0.25% gelatin (bloom 275) at room temperature. Blots were incubated with anti-phospho-STAT-6 antibodies overnight at 4° C. followed by horseradish peroxidase-conjugated bovine anti-rabbit secondary antibody for one hour. Immunoreactive bands were detected by enhanced chemiluminescence, ECLT™ (Amersham Life Sciences, San Francisco, Calif.), visualized and quantified on a FLUORCHEM™ 8000 Imaging System using ALPHAEASE™ software (Alpha Innotech, San Leandro, Calif.).

EXAMPLE 2

Splenocyte Culture and Cytokine Analysis

BALB/c mice were sensitized systemically by two weekly i.p. injections of 0.025% ovalbumin mixed with 4 mg/mL Al(OH)$_3$. One week after the second sensitization, mice were sacrificed and spleens harvested. A single cell suspension of splenocytes (5×10$^6$ cells/mL) was cultured in RPMI-1640 medium containing 10% heat-inactivated fetal bovine serum and 2 mM L-glutamine, 50 µM 2-mercaptoethanol, 100 U/mL penicillin, and 100 µg/mL streptomycin sulfate. Splenocytes were cultured for four days in the presence or absence of 100 µg/mL ovalbumin, either alone or with 100 µM STAT-6-IP or STAT-6-CP, which were added daily. After four days, culture supernatants were harvested to quantify cytokine production by ELISA. Murine IL-4 and IFN-gamma ELISA kits were purchased from BD PHARMINGEN™ (San Diego, Calif.) and murine IL-13 ELISA kit was purchased from BIOSOURCE® (Camarillo, Calif.). To monitor expression of cytokines by intracellular cytokine staining, splenocytes were cultured for five hours with murine anti-CD3 (0.5 µg/mL; clone 2C11) and monensin (GOLGISTOP™; BD PHARMINGEN™, San Diego, Calif.) according to the manufacturer's instructions. Cells were washed, permeabilized with saponin (PERM/WASH™; BD PHARMINGEN™, San Diego, Calif.), and fixed in formaldehyde and PBS (CYTOFIX/CYTOPERM; BD PHARMINGEN™, San Diego, Calif.) for 30 minutes. Splenocytes were stained with FITC-conjugated rat anti-mouse CD4, PE-conjugated rat anti-mouse IL-4, and APC-conjugated rat anti-mouse IFN-gamma, (all from BD PHARMINGEN™, San Diego, Calif.). Cytokine expression was monitored by flow cytometry and analyzed using CELLQUEST™ software (Becton Dickinson). Experiments were replicated independently three times and means reported.

Reverse transcriptase (RT)-PCR was used to monitor expression of mRNAs encoding IL-4, IL-13 and IFN-gamma. Materials for RNA extraction and RT-PCR were purchased from INVITROGEN™ Canada (Burlington, Ontario). Total RNA was extracted from splenocytes, treated with DNAse, and 1 µg of RNA was reverse transcribed into cDNA using SUPERSCRIPT™ II reverse transcriptase. The cDNA was PCR amplified as follows: 1 cycle of 94° C. for 2 minutes; 35 cycles of 45 seconds at 94° C., 30 seconds at 54° C., and 1.5 minute at 72° C.; and 1 cycle at 72° C. for 10 minutes. PCR products were resolved by gel electrophoresis and visualized and quantified on a FLUORCHEM™ 8000 Imaging System (Alpha Innotech, San Leandro, Calif.) using ALPHAEASE™ software (Alpha Innotech). The follow PCR primers were used: IL-4, 5'-GCT AGT TGT CAT CCT GCT C-3' (SEQ ID NO:16) and 5'-GTG ATG TGG ACT TGG ACT C-3' (SEQ ID NO:17); IL-13, 5'-GCC AGC CCA CAG TTC TAC AGC-3' (SEQ ID NO:18) and 5'-GTG ATG TTG CTC AGC TCC TCA-3' (SEQ ID NO:19); IFN-gamma, 5'-TGG CTC TGC AGG ATT TTC ATG-3' (SEQ ID NO:20) and 5'-TCA AGT GGC ATA GAT GTG GAA GAA-3' (SEQ ID NO:21); and GAPDH, 5'-GCC ATG GAC TGT GGT CAT GA-3' (SEQ ID NO:22) and 5'-TTC ACC ACC ATG GAG AAG GC-3' (SEQ ID NO:23).

EXAMPLE 3

Animals

Six-to-eight week-old male BALB/c mice were obtained from Harlan-Sprague Dawley (Indianapolis, Ind.) and were housed in a conventional animal facility. For each experimental condition, a minimum of 6-8 animals was used. Awake animals were sensitized five days per week for each of two weeks by instillation in each nostril of 5 µL 1% ovalbumin in PBS. Alternatively, animals were sensitized by two weekly systemic, i.p. injections of 0.025% ovalbumin mixed with 4 mg/mL Al(OH)$_3$. Following two weeks rest, animals were challenged for five days by intranasal instillation of 1% ovalbumin. Animals treated with peptides received the STAT-6-IP (15, 50, or 150 µg) or STAT-6-CP (50 or 150 µg) in 10 µL PBS 30 minutes prior to each ovalbumin challenge. Twenty-four hours after the last ovalbumin challenge, mice were deeply anaesthetized with xylazine and sodium pentobarbital and paralyzed with pancuronium bromide. The tail vein was cannulated for drug administration and heart rate was monitored by EKG. The trachea was exposed, a cannula inserted and secured with silk ties and then attached to a computer-controlled small-animal ventilator (FlexiVent; SCIREQ, Montreal, Quebec). Mice were ventilated quasi-sinusoidally with a tidal volume of 8 mL/kg and respiratory rate of 150 breaths/minute. Respiratory system resistance was measured. Airway hyperresponsiveness was by low dose methacholine. Methacholine was injected through the tail vein at dose of 10, 20, 40, 80, 160, 320 µg/kg and the maximal resistance and elastance were recorded. Afterward, the trachea was isolated and a 22-gauge stainless steel catheter was inserted into the proximal trachea and secured with 4-0 silk suture. The lungs were lavaged using 0.5 mL of ice cold 0.9% NaCl. The bronchoalveolar lavage (BAL) fluid was centrifuged to remove intact cells and the supernatant stored at −20° C. for IL-13 analysis by ELISA. Red blood cells (RBC) in the BAL fluid cell pellet were lysed and cells were spun onto glass slides, stained using Diff-quick (Fisher Scientific, Ottawa, Canada), and differential cell counts obtained manually under light microscopy. Six fields were counted, each encompassing 100 cells per slide, and means obtained.

EXAMPLE 4

Histological Analysis

Histology was performed according to established methods (McCusker, et al. (2002) supra). Briefly, lungs were slowly inflated with 1 mL of formalin, isolated, and placed entirely in formalin. The specimens were embedded in paraffin and 0.5 µm sections prepared. Slides were stained with Giemsa and examined under standard light microscopy.

EXAMPLE 5

Statistical Analysis

Results are expressed as mean±standard error of the mean. Statistical significance was measured by one-way ANOVA followed by Tukey's post hoc tests for individual group comparisons using SPSS software. Group comparisons as well as individual comparisons for each data set are provided.

What is claimed is:

1. An isolated chimeric STAT-6 peptide comprising a 4 to 40 amino acid residue portion of STAT-6 comprising Tyr-641 of SEQ ID NO:24 or SEQ ID NO:25, wherein said portion of STAT-6 is operably linked to a protein transduction moiety.

2. The isolated chimeric STAT-6 peptide of claim 1, wherein the portion of STAT-6 further comprises the three amino acid residues immediately C-terminal to Tyr-641.

3. A method for treating a STAT-6 associated disease or condition comprising administering an effective amount of the isolated chimeric STAT-6 peptide of claim 1 to a subject having or at risk of having allergic rhinitis, asthma or an immune disorder associated with transcriptional activation by STAT-6 dimer so that said allergic rhinitis, asthma or immune disorder is treated.

* * * * *

UNITED STATES PATENT AND TRADEMARK OFFICE
CERTIFICATE OF CORRECTION

PATENT NO. : 7,829,528 B2
APPLICATION NO. : 11/575164
DATED : November 9, 2010
INVENTOR(S) : Fixman et al.

Page 1 of 1

It is certified that error appears in the above-identified patent and that said Letters Patent is hereby corrected as shown below:

On Title Page section (73), please delete "The Rockefeller University, New York, NY (US)"

On Title Page section (73), please insert -- McGill University, Montreal, Quebec (CA) --

At column 35, line 14, claim 1, please delete "1. An isolated chimeric STAT-6 peptide comprising a 4 to 40 amino acid residue portion of STAT-6 comprising Tyr-641 of SEQ ID NO:24 or SEQ ID NO:25, wherein said portion of STAT-6 is operably linked to a protein transduction moiety."

At column 35, line 14, claim 1, please insert -- 1. An isolated chimeric STAT-6 peptide comprising a portion of STAT-6 operably linked to a protein transduction moiety, wherein said portion of STAT-6 comprises Tyr-641 of SEQ ID NO:24 or SEQ ID NO:25 and is 4 to 40 amino acid residues in length. --

At column 35, line 18, claim 2, please delete "2. The isolated chimeric STAT-6 peptide of claim 1, wherein the portion of STAT-6 further comprises the three amino acid residues immediately C-terminal to Tyr-641."

At column 35, line 18, claim 2, please insert -- 2. The isolated chimeric STAT-6 peptide of claim 1, wherein the portion of STAT-6 comprises at least Tyr-641 of SEQ ID NO:24 or SEQ ID NO:25 and the three amino acid residues immediately C-terminal to Tyr-641. --

Signed and Sealed this
Fifteenth Day of February, 2011

David J. Kappos
*Director of the United States Patent and Trademark Office*